United States Patent [19]

Dürsch et al.

[11] 4,250,124
[45] Feb. 10, 1981

[54] ORGANIC PHOSPHORUS COMPOUNDS POSSESSING 3-HYDROXYALKYLPHOSPHINIC ACID ESTER GROUPS

[75] Inventors: Walter Dürsch; Fritz Linke, both of Königstein; Hans-Jerg Kleiner, Kronberg, all of Fed. Rep. of Germany

[73] Assignee: Hoechst Aktiengesellschaft, Fed. Rep. of Germany

[21] Appl. No.: 78,135

[22] Filed: Sep. 24, 1979

[30] Foreign Application Priority Data

Sep. 27, 1978 [DE] Fed. Rep. of Germany ....... 2841941

[51] Int. Cl.³ .............................................. C07F 9/29
[52] U.S. Cl. ................................. 260/928; 260/931; 260/982
[58] Field of Search ........................ 260/928, 931, 982

[56] References Cited

U.S. PATENT DOCUMENTS 2,648,695  8/1953  Smith ................................. 260/936
2,916,510  12/1959  Garner ................................ 260/936

Primary Examiner—Anton H. Sutto
Attorney, Agent, or Firm—Connolly and Hutz

[57] ABSTRACT

Organic phosphorus compounds possessing 3-hydroxyalkylphosphinic acid ester groups of the formula

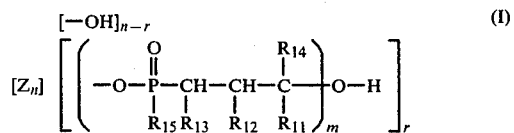

wherein the individual symbols have the meaning given in the description. These compounds have been obtained by reaction of compounds containing one or more hydroxyl groups with a 2-substituted 2-oxo-oxaphospholane. The products of the above formula are in particular suitable for use as flameproofing agents for textile material.

2 Claims, No Drawings

ORGANIC PHOSPHORUS COMPOUNDS POSSESSING 3-HYDROXYALKYLPHOSPHINIC ACID ESTER GROUPS

The demand for phosphorus compounds possessing crosslinkable hydroxyl groups has substantially increased in recent years. For example, for optimum permanent flame-retardant finishes, above all of textile floor coverings, water-soluble phosphorus compounds which are "made-to-measure" in accordance with the nature of the chemical substrate, and which possess particular low or high hydroxyl numbers, a high phosphorus content, and particular degrees of crosslinking, are required.

The invention relates to organic phosphorus compounds possessing 3-hydroxyalkylphosphinic acid ester groups of the general formula I $$[Z_n]\left[\left(-O-\overset{O}{\underset{\|}{P}}-\underset{R_{15}R_{13}}{CH}-\underset{R_{12}}{CH}-\underset{R_{11}}{\overset{R_{14}}{\underset{|}{C}}}\underset{m}{\longrightarrow}O-H\right)_r\right] \quad [-OH]_{n-r} \quad (I)$$

wherein the individual symbols in the above formula I have the following meaning:

n is an integer from 1 to 6, preferably 1 to 4;

r is an integer from 1 to n, that is to say from 1 to 6, and is preferably the same number as n;

m is 1 if $r < n$, or is a number from 1 to 150, preferably 2 to 10, if r is equal to n;

$R_{11}$, $R_{12}$, $R_{13}$ and $R_{14}$ are identical or different, optionally unsaturated and/or branched, alkyl radicals with 1 to 4 carbon atoms or, preferably, are hydrogen;

$R_{15}$ has the same meaning as $R_{11}$, other than hydrogen, and is preferably ($C_1$–$C_3$)-alkyl, and particularly preferentially methyl;

$Z_n$ is a n-valent radical from the group of straight-chain or branched aliphatic or araliphatic hydrocarbon radicals with 1 to 22, preferably 1 to 8, C atoms, which can optionally be interrupted by up to 2 -S- and/or $NR_2$— radicals, where $R_2$ is ($C_1$–$C_4$)-alkyl, especially methyl, and/or be substituted by fluorine, chlorine or bromine atoms or by optionally unsaturated carboxylic acid ester groups or carboxamide, carbamate or urea groups or by primary, secondary or tertiary amino groups; or is a hydrocarbon radical, containing ether groups, with equivalent weights of up to 8,000, preferably up to 4,000, resulting from oxyethylation and/or oxypropylation of n-valent aliphatic, araliphatic or aromatic hydroxyl compounds, amines and/or monocarboxylic or dicarboxylic acids with 1 to 22, preferably 1 to 10, C atoms, the araliphatic or aromatic radicals being derived from benzene, alkylbenzenes or alkylenebenzenes with up to 18 C atoms, naphthalene, diphenyl, diphenylmethane, diphenylethane or 2,2-diphenylpropane, and being optionally substituted in the nucleus by 1 or 2 methoxy or ethoxy groups, or optionally substituted, preferably up to five times, in the nucleus and/or in the side chains by F, Cl or Br atoms; or is a phosphorus-containing radical of the general formula $$R_2-(O)_{d_1}-\overset{R_1}{\underset{\underset{O}{\|}}{P}}-(O)_{d_1}-R_3 \quad Z_{n,1}$$

in which the indices $d_1$, independently of one another are 0 and 1 and $R_1$ is alkyl, hydroxyalkyl, optionally ($C_1$–$C_2$)-alkylated or -dialkylated aminoalkyl, halogenoalkyl (preferably Cl-alkyl) with 1 to 3 C atoms, alkenyl with 2 or 3 C atoms or phenyl, which can optionally be substituted by 1 or 2 halogen atoms, preferably Cl or Br, and $R_2$ and $R_3$ have the same meaning as $R_1$, with the restriction that at least one of the radicals $R_2$ or $R_3$ is an alkyl radical with 2–5 C atoms;

or is a phosphorus-containing radical of the formula $$\begin{array}{c} R_3-O \diagdown \qquad \diagup O-R_3 \\ \diagup P-R_4-P \diagdown \quad Z_{n,2} \\ R_2-(O)_{d_1} \overset{\|}{O} \qquad \overset{\|}{O} (O)_{d_1}-R_2 \end{array}$$

in which $d_1$, $R_2$ and $R_3$ have the same meanings as in $Z_{n,1}$ and $R_4$ denotes a straight-chain or branched ($C_1$–$C_{10}$)—

$$-\overset{R_5}{\underset{\underset{Y}{|}}{C}}-,$$

alkylene, phenylene or xylylene radical or a radical where Y is OH or $NH_2$ and $R_5$ is ($C_1$–$C_3$)-alkyl; or is a phosphorus-containing radical of the general formula $$-CHR_{10}-CHR_9-O-\overset{}{\underset{\underset{O}{\|}}{C}}-CHR_7-CHR_8-\overset{R_6}{\underset{\underset{O}{\|}}{P}}-O-CHR_9-CHR_{10}Z_{n,3}$$

in which $R_6$ denotes a ($C_1$–$C_4$)-alkyl group which can optionally be substituted, preferably monosubstituted, by halogen, especially chlorine, a cycloalkyl group with up to 8 C atoms, especially cyclopentyl or cyclohexyl, an alkylene group with up to 4 C atoms, especially vinyl and allyl, or a phenyl or benzyl group which is optionally substituted, preferably monosubstituted, disubstituted or trisubstituted, by halogen, preferably chlorine and/or bromine, $R_7$ denotes hydrogen or a ($C_1$–$C_4$)-alkyl group, preferably methyl, $R_8$ denotes hydrogen or a ($C_1$–$C_2$)-alkyl group, preferably methyl, but at least one of the radicals $R_7$ and $R_8$ is hydrogen, $R_9$ denotes hydrogen, methyl or chloromethyl and $R_{10}$ denotes hydrogen, methyl or ethyl, preferably hydrogen.

The compounds of the formula I are obtained if 1 mole of a compound of the general formula II $$Z_n(OH)_n \qquad (II)$$

is reacted with 1 to n.25 moles of 2-substituted 2-oxo-oxa-phospholanes of the general formula III

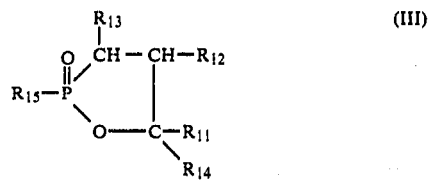

wherein n, $R_{11}$, $R_{12}$, $R_{13}$, $R_{14}$ and $R_{15}$, and $Z_n$, have the meanings given above.

The alcohols of the formula II, $Z_n(\text{---OH})_n$, are all accessible in accordance with known methods. Amongst the usable monohydric oganic hydroxyl compounds, with n = 1, it is possible to employ, for example, all easily accessible aliphatic, straight-chain or branched, alcohols with 1 to 22 C atoms. As the most important, there may for example be mentioned methanol, ethanol, n-propanol, i-propanol, n-butanol, sec.-butanol, n-hexanol, 2-ethyl-butan-1-ol, n-octanol, 2-ethyl-hexan-1-ol, n-do-decanol, n-hexadecanol and n-octadecanol, amongst which the alcohols with 1 to 4 C atoms are preferred. Polyhydric alcohols with n=2-6 are even more suitable than monofunctional alcohols.

Amongst the polyhydric aliphatic polyols with n=2-6, there may be mentioned, for example, ethylene glycol, 1,2-propylene glycol, 1,3-propylene glycol, 1,4-butanediol, neopentylglycol, 1,6-hexanediol, glycerol, tris-hydroxymethylethane, tris-hydroxymethylpropane, pentaerythritol, sorbitol and mannitol. Glycerol and 1,4-butanediol are particularly suitable.

Amongst unsaturated alcohols there may, for example, be mentioned n-but-2-en-1-ol, butene-1,4-diol and allyl alcohol, butene-1,4-diol being the preferred dihydric alcohol.

Amongst the numerous compounds in which one or more —CH$_2$— groups in an aliphatic hydrocarbon radical are replaced by ether bridges —O—, examples of suitable compounds are the reaction products of monohydric alcohols with one or more molecules of alkylene oxides or alkylene carbonates, such as, for example, 2-methoxyethanol, 2-ethoxyethanol, 2-n-butoxy-ethanol, 2-(2'-ethyl-hexyloxy)-ethanol and 2-n-dodecyloxy-ethanol, as well as the reaction products of 1 mole of methanol, 1 mole of ethanol and 1 mole of isopropanol with 2 moles of ethylene oxide or ethylene carbonate ie. the so-called methyldiglycol, ethyldiglycol and isopropyldiglycol, as well as reaction products of 3 to 100 moles of ethylene oxide or ethylene carbonate with 1 mole of methanol, ethanol, isobutanol, dodecanol, oleyl alcohol and the like.

Suitable reaction products of ethylene oxide with dihydric alcohols are, for example, the so-called diglycol, the so-called triglycol and the higher reaction products of ethylene oxide and/or ethylene carbonate with water or ethylene glycol, namely the so-called polyethylene glycols of various molecular sizes up to a mean molecular weight of 8,000, but especially diglycol and triglycol; further suitable compounds are, for example, the adducts of 1 to 150 molecules of ethylene oxide and/or ethylene carbonate with trihydric or polyhydric alcohols (n=3-6), such as, for example, glycerol, tris-hydroxymethylpropane, pentaerythritol and the like.

In addition to reaction products of ethylene oxide and/or ethylene carbonate with monohydric or polyhydric alcohols, it is also possible to use reaction products of monohydric and polyhydric alcohols with other 1,2-alkylene oxides and/or 1,2-alkylene carbonates, such as, above all, 1,2-propylene oxide, 1,2-propylene carbonate or epichlorohydrin, as well as the reaction products of ethylene oxide and/or ethylene carbonate with poly-1,2-propylene glycols, which, as is known, are surface-active compounds which can be prepared with many variations. Compounds to be mentioned particularly are the appropriate poly-1,2-propylene glycols and appropriate adducts of ethylene oxide and/or ethylene carbonate with poly-1,2-propylene glycols with molecular weights of up to 8,000, preferably up to 4,000.

In addition to being interrupted by —O— bridges, the hydrocarbon chain of aliphatic hydroxyl compounds can also be interrupted or substituted by other heteroatoms, such as, for example, by the elements N, S and/or P or carboxylic acid ester groups. These compounds can, for example, be obtained particularly simply by reacting one or more molecules of 1,2-alkylene oxides and/or 1,2-alkylene carbonates with ammonia, primary or secondary amines, hydrogen sulfide, mercaptans, oxyacids of phosphorus, (C$_2$-C$_6$)-carboxylic acids or dicarboxylic acids.

Amongst the reaction products with 1,2-alkylene oxides or 1,2-alkylene carbonates there may, for example, be mentioned the following:

Products with N in the molecule; monoethanolamine, diethanolamine, di-propanol-2-amine, tertiary alkanolamines, such as, for example, triethanolamine, methyldiethanolamine, n-butyl-diethanolamine, tetrahydroxyethylethylenediamine, pentahydroxyethyl-diethylenetriamine, n-dodecyldiethanolamine, dimethylethanolamine, n-butylmethylethanolamine, di-n-butyl-ethanolamine, n-dodecylmethylethanolamine and corresponding higher reaction products of these tertiary amines with up to 150 moles of ethylene oxide or ethylene carbonate or propylene oxide or propylene carbonate.

Products with S in the molecule: bis-(2-hydroxyethyl)-sulfide, bis-(2-hydroxypropyl)-sulfide, bis-(2-hydroxyethyl)-sulfone and their reaction products with further ethylene oxide or ethylene carbonate or propylene oxide or propylene carbonate, having molecular weights of up to 8,000.

Products with P in the molecule: neutral reaction products of 1,2-alkylene oxides, such as ethylene oxide or propylene oxide, or epichlorohydrin, above all of ethylene oxide, or of ethylene carbonate, with monobasic or polybasic alkanephosphonic acids with 1 to 18 C atoms, such as, for example, with n-butane-, isobutane-, 2-ethylhexane-, n-octane-, decane-, dodecane- and tetradecanephosphonic acid, but especially with methane-, ethane-, propane- and vinyl-phosphonic acid and 1,2-ethanediphosphonic acid, as well as with monobasic or polybasic dialkyl-phosphinic acids, such as, for example, methylbutyl-phosphinic acid, methyl-n-octyl-phosphinic acid, methyl-n-dodecyl-phosphinic acid and especially dimethyl-, ethyl-methyl-, methyl-propyl- and methyl-vinyl-phosphinic acid and ethane-1,2-bis-(methyl-phosphinic acid), and also reaction products of 1 to 7 moles of alkylene oxide or ethylene carbonate with monobasic aliphatic carboxylic acids, such as, for example, crotonic acid and above all acetic acid, propionic acid or butyric acid, and with polybasic aliphatic carboxylic acids, such as, for example, succinic acid and adipic acid.

In addition to such hydroxyl compounds with N, S and P hetero-atoms, which are very easily accessible by oxyalkylation reactions, numerous other compounds with hydroxyl groups and optionally with these hetero-atoms and/or carboxylic acid ester groups in the hydrocarbon chain are suitable, amongst which oligo-condensates produced by reaction of dicarboxylic acids with polyhydric alcohols, methyl glycolate, ethyl 2-hydroxyethane-carboxylate and the like are only some examples.

Additional suitable compounds are, for example, hydroxymethane-phosphonic acid dimethyl ester, 2-hydroxyethane-phosphonic acid diethyl ester, 3-hydroxypropane-phosphonic acid di-n-butyl ester and the like, and analogous compounds from the phosphinic acid series, such as, for example, hydroxymethyl-methyl-phosphinic acid methyl ester, 2-hydroxyethyl-methyl-phosphinic acid ethyl ester, 3-hydroxypropyl-methyl-phosphinic acid 2'-ethyl-hexyl ester, hydroxymethyl-dimethyl-phosphine oxide and 2-hydroxyethyl-dimethyl-phosphine oxide.

All the aliphatic hydroxyl compounds mentioned, and analogous compounds not mentioned, can be substituted by the halogen atoms chlorine, bromine and fluorine, especially by chlorine or bromine. Examples which may be mentioned are the following compounds, which are easily accessible and are of interest because of their advantageous flameproofing characteristics: 2-bromoethanol, 2,3-dibromopropan-1-ol, 2,3-dibromobutane-1,4-diol, dibromosuccinic acid bis-(2-hydroxyethyl) ester, 2,3-dibromopropane-phosphonic acid bis-(2-hydroxyethyl) ester, 2-hydroxyethanephosphonic acid bis-(2,3-dibromopropyl) ester, chloroethanol, 2,3-dichloro-propan-1-ol, 1,3-dichloro-propan-2-ol, 2,3-dichloro-butane-1,4-diol, 2-hydroxyethanephosphonic acid bis-(2,3-dichloropropyl) ester, 1-chloro-vinylphosphonic acid bis-(2-hydroxyethyl) ester and the like.

The available range of suitable aromatic compounds containing ether groups and n OH radicals is also very diverse. It is possible to use all oxyalkylation products of so-called phenols in the broader sense, such as, for example, phenol, pyrocatechol, resorcinol, hydroquinone, pyrogallol, hydroxyhydroquinone, phloroglucinol, the various tetrahydroxybenzenes and pentahydroxybenzenes, hexahydroxybenzene, α-naphthol, β-naphthol, hydroxynaphthalenes with more than one hydroxyl group, such as, for example, 1,2-, 1,3-, 1,4-, 1,5-, 1,6-, 1,7-, 1,8- and 2,3-dihydroxy-naphthalene, 4-hydroxydiphenyl, 4,4'-dihydroxydiphenyl and - because of its advantageous price - above all, 2,2-bis-(4-hydroxyphenyl)-propane and 4,4'-bis-(4-hydroxyphenyl)-methane, the oxyalkylation products having molecular weights of up to 8,000. The oxyalkylates of partially etherified polyhydric aromatic hydroxyl compounds, such as, for example, hydroquinone monomethyl ether, resorcinol monoethyl ether and the like are also suitable.

Because of the advantageous effect on flameproofing properties, aromatic chloro-hydroxy compounds and especially bromo-hydroxy compounds are of particular interest, such as, for example, the 2-hydroxy-ethyl ethers of 2,4,6-tribromophenol, pentabromophenol, 2,4,6-trichlorophenol or pentachlorophenol and of 2,2-bis-(4-hydroxy-3,5-dibromophenyl)-propane.

Other suitable compounds are the oxyalkylates of aromatic hydroxy compounds having alkyl side groups with a total of up to 18 C atoms, such as, for example, the oxyalkylates of o-, m- or p-cresol, thymol, 4-tert.-butylphenol, n-nonylphenol and isotridecylphenol, the oxyalkylates having molecular weights of up to 8,000.

Further suitable examples amongst the araliphatic and aromatic compounds are all araliphatic compounds with alcoholic hydroxyl groups, such as, for example, benzyl alcohol, and all 2-hydroxyalkyl esters which are formed by oxyalkylation reactions of aromatic compounds which contain free carboxylic acid, phosphonic acid or phosphinic acid radicals.

For the preparation of aromatic starting materials II having alcoholic hydroxyl groups, suitable compounds for the reaction with 1,2-alkylene oxides or 1,2-alkylene carbonates, in addition to the aromatic compounds with phenolic hydroxyl groups which have already been mentioned, are therefore, above all, aromatic monocarboxylic and dicarboxylic acids, such as, for example, benzoic acid, phthalic acid, isophthalic acid, terephthalic acid, 1-naphthalenedicarboxylic acids and also aromatic hydroxycarboxylic acids, such as, for example, the three different hydroxybenzoic acids, the different naphtholcarboxylic acids, 4,4'-diphenyl-dicarboxylic acid and the like.

Equally suitable compounds are, for example, all other aromatic carboxylic acids which are derived from benzene and naphthalene and contain bromine, chlorine or fluorine, such as above all, for example, tetrabromonaphthalic acid and tetrachloronaphthalic acid.

Equally, aromatic phosphonic acids and phosphinic acids, such as, for example, benzenephosphonic acid, 1,3- and 1,4-phenylene-diphosphonic acid, phenyl-methyl-phosphinic acid, 1,3- and 1,4-phenylene-bis-(methyl-phosphinic acid) and the like can be converted to the corresponding 2-hydroxyalkyl esters by reaction with the 1,2-alkylene oxides and/or 1,2-alkylene carbonates.

Suitable aromatic compounds with alcoholic hydroxyl groups can, however, also be obtained by prior reaction of aromatic amines or mercapto compounds with 1,2-alkylene oxides and/or 1,2-alkylene carbonates.

As compounds containing aromatic amino groups suitable for oxyalkylation reactions there may for example be mentioned aniline, methylaniline, o-, m- and p-phenylenediamine, the various o-, m- and p-toluidines, -anisidines, -aminophenols and -aminobenzoic acids, naphthylamines, the various amino-naphthols, 4,4'-diaminodiphenylmethane, 4,4'-benzidine, the possible chloroanilines and bromanilines and above all 2,4,6-tribromoaniline and the like, but also phenylalkylamines, such as, above all, benzylamine or methylbenzylamine, and dibenzylamine.

As aromatic mercapto compounds which can be oxyalkylated there may for example be mentioned: phenylmercaptan, p-toluyl-mercaptan, 1- and 2-naphthylmercaptan and the like.

Amongst all compounds II with alcoholic hydroxyl groups, particularly preferred compounds are those which in addition contain crosslinkable methylolizable or polymerizable radicals, such as, for example, 2-hydroxyethyl carbamate, 2-hydroxyethyl-urea, 2-hydroxyethyl methacrylate and the like.

It is possible to employ only one compound of the formula II at a time, but it is also possible to use mixtures of several compounds II. Corresponding mixtures of the compounds I are then obtained.

The 2-substituted 2-oxo-oxa-phospholanes of the formula III can be obtained, for example, by addition reaction of methanephosphonous acid esters of the formula IV

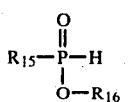

wherein $R_{16}$ denotes an alkyl radical with 1–6, preferably 1–4, carbon atoms, with monohydric unsaturated alcohols of the general formula V

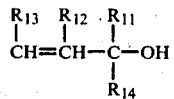

in the presence of radical donors, at temperatures of about 130°–170° C. The 3-hydroxyalkyl-alkylphosphonic acid alkyl esters of the general formula VI

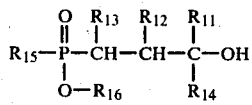

which are first produced by this reaction are converted, on heating, to the 2-substituted 2-oxo-oxa-phospholanes III, with elimination of alcohols of the formula VII

 (VII)

A large number of suitable compounds III results from the combination of the different variable radicals $R_{14}$, $R_{13}$, $R_{12}$ and $R_{11}$.

Specific examples of suitable compounds III are:

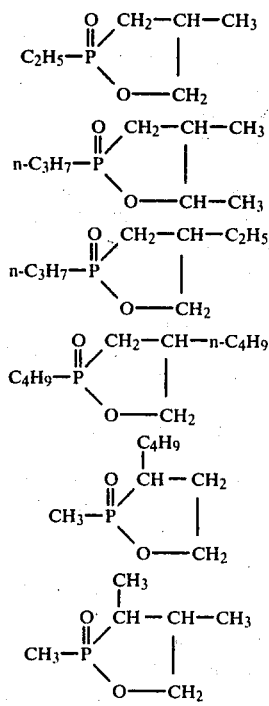

preferably

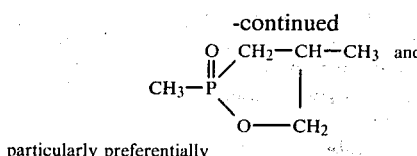

particularly preferentially

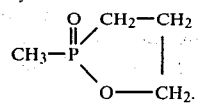

It is possible to use only one compound of the formula III at a time. However, it is also possible to use mixtures of several compounds of the formula III. In that case mixtures of the compounds of the formula I are obtained.

The molar ratios of the 2-substituted 2-oxo-oxaphospholanes III to the alcohols II can vary within wide limits, depending on the desired phosphorus content and hydroxyl group content. The molar ratios can be between 1/n and n.m. This means that 1 mole of an alcohol $Z_n(-OH)_n$ can be reacted with 1 to m.n (or 150 n) moles of III. The larger is m, the higher is the P content of the reaction product and the lower the content of hydroxyl groups or the "hydroxyl number"(OH-number). Per hydroxyl group, a maximum of up to m=150 moles, preferably m=2–8 moles, of III can be added on.

The reactions of the compounds II and III must be carried out in the absence of water. In many cases, above all if the compounds II and III are liquids of low viscosity, the use of solvents is superfluous. However, if the compounds II and/or III are substances which are solid at the chosen reaction temperatures, it is advisable to add anhydrous inert, relatively polar solvents or diluents, which should be as volatile as possible, such as above all, for example, tetrahydrofuran, dioxane, acetone, 1,2-dimethoxy-ethane, acetonitrile and the like. After carrying out the reactions, these solvents or diluents must be removed again under very gentle conditions - if appropriate in vacuo.

The reaction can also be carried out in the absence of catalysts. However, alkaline catalysts greatly accelerate the reaction. Suitable strongly alkaline catalysts are in particular the alkali metals lithium, potassium and preferably sodium, sodium amide and preferably sodium hydride and alkali metal alcoholates, such as above all, sodium ethylate and—because of causing little discoloration—sodium methylate in the form of highly concentrated solutions in methanol. For example, the alcoholates of the alcohol II employed, which alcoholates are outstandingly suitable alkaline catalysts, can be produced very conveniently by mixing the sodium methylate solution with the compounds I and stripping off the methanol in vacuo at as low a temperature as possible. Weakly alkaline catalysts, such as, for example, sodium carbonate or potassium carbonate, only accelerate the reaction at elevated temperatures of about 60°–200° C.

The molar amounts of alkali metal catalysts depend in particular on the number of moles of compounds III.

Per mole of the compounds III, it is advisable to employ 0.002–0.5 mole, preferably 0.01 to 0.2 mole, of alkali catalysts.

A part of the alkali catalyst is consumed by sidereactions, above all by saponification of phosphinic acid ester groups. In order to detect whether sufficient amounts of free alkali are still present, it is advisable to add indicators, preferably indicators which are colorless in the neutral region, such as, for example, phenolphthalein or, preferably, thymolphthalein.

If required, excess free alkali can be neutralized after completion of the reaction by adding calculated amounts of inorganic or organic acids, or acid donors, such as, for example, sulfuric acid, phosphoric acid, ethanephosphonic acid, acetic acid, oxalic acid, acetic anhydride and the like.

The reaction temperatures can vary between about −10° C. and 200° C. They are very dependent on whether alkali catalysts are used at all, and on whether the reaction medium is alkaline or not. Preferred temperature ranges are 100° C. to 170° C. in the absence of catalysts and 10° C. to 60° C. in the presence of strongly alkaline catalysts, that is to say in an alkaline medium. The reaction times are 1 minute to about 48 hours, preferably 5 minutes to 20 hours. At higher temperatures, especially in the absence of alkali catalysts or in a neutral or sightly acidic pH range, substantially longer reaction times, preferably of about 1 to 20 hours, are necessary. In the presence of strong alkali catalysts, 5 minutes to 2 hours preferentially suffice. Under these conditions the reaction is in part highly exothermic, especially if small molecules of II and III are employed, so that during the addition of III to II intensive cooling may be necessary, and it is particularly advisable to add the compounds III in portions to the mixtures of the alcohols II and the corresponding alcoholates. Admittedly, it is also possible to mix the compounds II and III and to add solutions of alkali catalysts (for example sodium methylate solutions in methanol) dropwise. However, in that case there is always the danger of overheating of the reaction mixture and/or of (mostly undesirable) saponification reactions of a substantial proportion of phosphinic acid ester groups. Similar remarks apply to cases where only the 2-substituted 2-oxo-oxa-phospholanes III are initially introduced into the reaction vessel and the alcohols II are introduced slowly, as a mixture with, or simultaneously with, the alkali catalysts. At low reaction temperatures, the reaction is always interrupted if the pH value falls below about 5–7 (measured with moist indicator paper).

The reaction products obtained, of the formula II, are in most cases colorless oils but sometimes, for exaple when using longer-chain saturated fatty alcohols, are also pasty or waxy. Their hydroxyl numbers (=mg of KOH per gram) can vary within wide limits, namely between about 10 and about 900, preferably between 40 and 300.

It is noteworthy that in the preferred method of preparation, that is to say in the alkaline pH range, the addition reaction of the compounds III and the alcohols II takes place very smoothly and completely even at relatively very low reaction temperatures and that, furthermore, primary and secondary amino groups do not react. As a result, it is possible also to employ alcohols II which contain any desired amino groups, or which contain radicals which do not withstand heat, such as, for example, methacrylate, carbamate and urea radicals and the like.

The compounds of the formula I are valuable intermediate products for numerous phosphorus-organic compounds. In this context, an additional fact of particular interest is that even those alcohols of the formula II which by nature are not water-soluble, for example as a result of the presence of a relatively long-chain alkyl group, can be converted into water-soluble adducts by reaction with low-molecular compounds of the formula III. However, the compounds I can also be used directly as flameretardant agents for textile material, above all if the compounds are derived from low-molecular polyhydric or monohydric crosslinkable aliphatic alcohols. For this purpose, the compounds are fixed onto the textile material with reactive crosslinking agents, if appropriate in the presence of crosslinking catalysts, in accordance with known methods. An excellent flame-retardant effect is obtained in this way.

Since the compounds I according to the invention contain terminal hydroxyl groups they can be permanently crosslinked with polyfunctional N-methylol compounds of melamine, urea or cyclic urea compounds, in the presence of acid catalysts. If, on the other hand, the compounds I contain terminal vinyl groups, they can be polymerized or copolymerized respectively, together with other, or without other, compounds containing vinyl groups, in the presence of a polymerizaton catalyst. The high-polymer compounds obtained in this manner are also distinguished by good permanence on various textile materials.

Examples of suitable crosslinking polyfunctional N-methylol compounds are derivatives of amino-1,3,5-triazines, such as trimethylolmelamine, hexamethylolmelamine, trimethylolmelamine trimethyl ether, hexamethylolmelamine pentamethyl ether, trimethylolmelamine triisobutyl ether and dimethylol-acetoguanamine, as well as derivatives of urea, such as dimethylolurea, dimethylolurea dimethyl ether, dimethylolurea dibutyl ether, dimethylolcycloethyleneurea, dimethylolcyclopropyleneurea, dimethylol-4-methoxy-5-dimethyl-propyleneurea, dimethylol-5-hydroxy-propyleneurea, 1,3-dimethylol-4,5-dihydroxyimidazolid-2-one, 1,3-dimethylol-5-hydroxy-ethylhexahydrotriazin-2-one, dimethylolurone and dimethylol carbamates, such as, for example, dimethylolmethyl carbamate, dimethylolhydroxyethyl carbamate and dimethylolmethoxyethyl carbamate.

Interesting compounds which have proved particularly suitable are the melamine derivatives, for example trimethylolmelamine trimethyl ether or hexamethylolmelamine pentamethyl ether.

As catalysts which exhibit their action in the acid pH range, there are in general added about 0.2 to 5% by weight, preferably 0.4 to 3% by weight, of inorganic or organic acids, or salts of these which as a result of hydrolysis or as a result of a heat treatment liberate acid, such as, for example, sulfuric acid, hydrochloric acid, phosphoric acid, trichloroacetic acid, maleic acid, tartaric acid, citric acid, acetic acid or salts of these with ammonia, amines or polyvalent metals, preferably salts of strong or medium-strong acids, such as ammonium sulfate, ammonium chloride, monoammonium oxalate, diammonium oxalate, ammonium nitrate, magnesium chloride, aluminum chloride, zinc chloride, zinc nitrate, zinc fluoborate and 2-amino-2-methyl-propanol hydrochloride.

The crosslinking catalysts can be added individually, or as mixtures with one another, to the finishing liquors. Such finishing liquors, which are preferably aqueous, in general contain 2 to 5% by weight, preferably 2.5 to 4.5% by weight, of compounds of the formula I, as well as 5 to 10% by weight, preferably 7 to 9% by weight, of crosslinking substances, such as mentioned above, and also 0.2 to 5% by weight of crosslinking catalysts, as well as, optionally, 5 to 25% by weight of high polymers, preferably in the form of dispersions.

If the phosphorus compounds according to the invention contain vinyl groups, they are distinguished by a good capacity to polymerize on textile substrates of various compositions. The polymerization takes place even without using an inert protective gas, and in the presence of atmospheric oxygen, on textile substrates under conditions employed in textile technology, even if the substrate surface is very large. The polymers obtained in this manner impart very good flame protection to a great diversity of textile sheet-like structures. In general, radical donors are added to the finishing liquors as polymerization catalysts. It is, however, also possible to produce radicals on the fiber material by, for example, a treatment with high-energy rays.

The polymerization catalysts used are the compounds known for use in the polymerization of acrylates. For aqueous finishing liquors this means, for example, potassium or ammonium peroxide-sulfate (persulfate), hydrogen peroxide or hydrogen peroxide donors such as $NH_4P_2O_7.H_2O_2.H_2O$ or $(NH_2CONH_2).H_2O_2$ (referred to in the examples as carbamide-hydrogen peroxide), as well as redox catalyst systems, such as hydrogen peroxide and ascorbic acid or sodium bisulfite, manganese(III) chloride or iron(II) chlorife and sodium sulfite, sodium chlorate/sodium bisulfite, and sodium peroxide-sulfate/sodium bisulfite.

To increase the permanence, especially the wash resistance, of the flameproofing effect achieved according to the invention, it is particularly advantageous to add to the monomers of the formula I additional comonomers, especially those which have a crosslinking action. Examples of such comonomers are, above all, acrylamide, N-methylol-acrylamide, methylene-bis-acrylamide, N-methylol-methlene-bis-acrylamide, N,N'-dimethylolmethylene-bis-acrylamide, N-formamidomethyl-acrylamide, divinylbenzenes, triallyl cyanurate, imides and anhydrides of acrylic acid and of methacrylic acid, and 1,3,5-triazine. If comonomers which contain —C=C— groups, and which also possess other reactive groups, for example acrylamide or compounds containing N-methylol groups, such as, for example, N-methylol-methylene-bis-acrylamide or N,N'-dimethylol-dimethylene-bis-acrylamide, are used, yet further or additional crosslinking components can be added to the system, such as, for example, derivatives of amino-1,3,5-triazines, such as trimethylolmelamine, hexamethylolmelamine, hexamethylolmelamine pentamethyl ether and derivatives of urea, such as dimethylolurea, dimethylolurea dimethyl ether, dimethylolcycloethyleneurea, dimethylolcyclopropyleneurea, as well as dimethylol carbamates, for example dimethylolmethyl carbamate, dimethylolethyl carbamate and the like.

In total, these additions to the monomers of the formula I amount to 10–300 parts by weight, preferably 30–180 parts by weight, especially 40–120 parts by weight , per 1,000 parts by weight of substrate.

The textile fiber goods on which the flameretardant finishing operations can be carried out in accordance with the crosslinking possibilities described above, either by a condensation process or by a polymerization process, vary. Suitable goods are woven fabrics, knitted fabrics, nonwoven fabrics, for example needle-punched nonwovens for wall coverings and floor coverings, and tufted or woven carpets. Woven and knitted fabrics can consist of natural or regenerated cellulose fibers or of synthetic fibers, and, for example, needle-punched nonwoven carpeting can consist of 100% polyamide 6 fibers or of 50/50 polyester/polyamide fibers, or can have a polyester base (underside) and an upper face of polyamide 6 fibers, of 50/50 polyamide fibers/viscose rayon or of 50/50 polyester fibers/viscose rayon, or can consist of 100% polyester fibers.

Good permanent flameproofing effects are also achieved on fibrous goods which consist of 100% polypropylene fibers or of mixtures of polypropylene fibers with, for example, polyester, polyamide or cellulose fibers.

Very good flame-retardent effects are also achieved if the flame-retardant organo-phosphorus compounds, together with the abovementioned crosslinking products and catalysts, are incorporated into a preliminary impregnating liquor in the case of tufted carpets, or a backing finish liquor for woven carpets.

The base fabric of the tufted carpets can consist of cotton, jute, rayon, wool or synthetic fibers based on polyamide, polyester or polypropylene, or of mixtures, or of glass fibers. Needle-punched nonwovens made from polyester or polypropylene fibers are also excellent as base fabrics. The tufted pile (which may be a loop pile or cut pile) can consist of polyamide, polyester or polyacrylonitrile fibers. Mixtures of polyacrylonitrile fibers with, for example, 20% of polyester fibers have also proved suitable.

To obtain a pleasant hand, to achieve good dimensional stability, or to improve the abrasion and tread resistance of needle-punched nonwoven carpeting, high-polymer plastic dispersions are added to the finishing liquors.

In tufted goods, the pile threads are bound in the base fabric described above by a so-called pre-coat of high-polymer plastic dispersions to which the flame-retardant components according to the invention, crosslinking agents and catalysts are added.

Suitable plastic dispersions are polyvinyl acetate, polyvinyl acetate containing plasticizers, such as dibutyl phthalate, copolymers of vinyl acetate with dibutyl maleate or of vinyl acetate with ethylene, terpolymers of vinyl acetate with ethylene and vinyl chloride, of vinyl acetate with ethylene and acrylamide or of vinyl acetate with ethylene and N-methylolacrylamide, copolymers of butyl acrylate with N-methylolacrylamide, copolymers of butyl acrylate, N-methylolacrylamide and acrylic acid, copolymers of butyl acrylate, N-methylolacrylamide and/or N-methylolmethacrylamide and acrylic acid, copolymers of butyl acrylate, methyl methacrylate and methylolmethacrylamide, copolymers of butyl acrylate, acrylonitrile, N-methylolacrylamide and methacrylic acid, copolymers of butyl acrylate, acrylonitrile, N-methylolmethacrylamide and acrylic acid, copolymers of butyl acrylate, styrene, acrylonitrile and N-methylolmethacrylamide, copolymers of N-methylolmethacrylamide, butanediol diacrylate, methyl acrylate and butyl acrylate, copolymers of ethyl acrylate, acrylonitrile and N-methylolacrylamide, copolymers of butyl acrylate, vinyl acetate and N-methylolacrylamide, copolymers of butyl acrylate, acrylonitrile and N-methylolacrylamide, copolymers of styrene, butyl acrylate and acrylic acid, natural latex or synthetic latices of styrene-butadiene copolymers.

Preferred polymer dispersions are 50% strength polyvinyl acetate dispersions, copolymers of vinyl acetate/dibutyl maleate, for example in the ratio of 77/23, copolymers of vinyl acetate/ethylene, for example in the ratio of 84/16 or 75/25, copolymers of vinyl acetate/ethylene/vinyl chloride, for example in the ratio of 51/15/34, copolymers of vinyl acetate/ethylene/acrylamide in the ratio of 80/18/2, copolymers of vinyl acetate/ethylene/N-methylolacrylamide in the ratio of 77/18/5, copolymers of styrene/butyl acrylate/acrylonitrile/methacrylic acid/acrylamide, for example in the ratio of 16:61:25:2:1 or 25:53:25:2:1, copolymers of ethyl acrylate/acrylonitrile/N-methylacrylamide in the ratio of 6:3:1, copolymers of butyl acrylate/vinyl acetate/N-methylolacrylamide, 50% strength polyvinyl alcohol dispersions, 25% strength polyvinyl acetate dispersions, 25% strength polyethylene dispersions or approx. 50% strength butadiene-styrene latex, for example with a butadiene:styrene ratio of 40:60 or 35:60 (with an additional 3.5 parts of acrylic acid).

Such plastic dispersions are also used as a backing finish for woven carpets, in order to give the carpet a firmer hand.

In the case of tufted carpets, the back in general subsequently receives an additional coating with natural latex or a synthetic latex, for example based on a 40:60 or 60:40 butadiene:styrene copolymer, or a 35:60 butadiene:styrene copolymer additionally containing 3.5 parts of acrylic acid, or with polyurethanes of various compositions.

The finishing liquors, both for the pre-coat and for coating the back of woven carpets, additionally contain thickeners. As is known, the thickener serves the purpose of bringing the finishes physically to a condition which ensures that the impregnating liquors, when applied, do not strike through into the pile threads and cause these to stick together. Suitable thickeners are water-soluble hydroxyethyl celluloses, methylcelluloses, carboxymethylcelluloses, water-soluble starch products, partially etherified or completely etherified starch products, polyvinyl alcohols and the sodium or ammonium salts of alginic acid.

The pre-coat, or, in the case of woven carpets, the coating of the carpet back, can additionally contain chalk as a filler.

The process according to the invention, for the flame-retardant finishing of woven fabrics, knitted fabrics, nonwoven fabrics and tufted or woven carpets is carried out under application conditions customary in the textile industry. An additional process step is not required.

The flame-retardant finishing liquors can be applied by padding, by coating using a doctor, or by slop-padding. The process chosen depends on the textile goods. Woven fabrics or knitted fabrics are in general subjected to a padding treatment. Needle-punched nonwovens can be treated on a padder, or be finished by doctor-coating or slop-padding.

The pre-coat impregnating liquor, or the finish for the back of woven carpets, is applied by means of an air-knife, a knife-on-blanket coater or a doctor roller.

The coating is then dried and condensed. Cotton fabrics are first subjected to a pre-drying treatment at 80°–120° C. and then dried for 4–5 minutes at 140°–160° C. Needle-punched nonwovens, tufted carpets or woven carpets are dried at 130°–150° C.

The finishing liquors may contain additional finishing agents such as textile softeners, hydrophobic agents, oleophobic agents or antimicrobial finishing products.

PREPARATION EXAMPLES
PRELIMINARY REMARKS

2-Methyl-2-oxo-oxa-phospholane

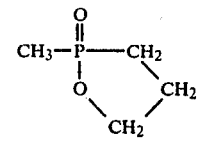

(abbreviated to MOP) gives, in a $^1$H noise-decoupled 40.5 MHz 31-P-NMR spectrum, a characteristic signal at $-71$ ppm, relative to trimethyl phosphite as internal standard (CDCl$_3$ as the solvent). All the reaction products described in the examples no longer show this signal or at most show it at a negligible intensity of at most about 3%. The hydrolysis numbers quoted were not determined in the usual way with phenolphthalein as an indicator, that is to say at a pH value of about 9.3–9.4, but were determined potentiometrically at a pH value of 8.0. This was necessary since the reaction products in part hydrolyze in the alkaline range, or are prone to alcoholysis, and as a result can under certain circumstances simulate hydrolysis numbers which are far too low.

In all cases, nitrogen is passed over the reaction mixture to exclude water and air.

EXAMPLE 1: (n=1, m=2)

0.24 g (0.001 mole) of sodium hydride and a small amount of thymolphthalein as the indicator are introduced into 26.8 g (0.1 mole) of oleyl alcohol at 60° C. The mixture is stirred for 60 minutes. 24 g (0.2 mole) of MOP are then added dropwise at 20° C. in the course of 10 minutes, whilst cooling, after which stirring is continued for 1 hour. This causes the originally blue solution to lose its color. A pale yellowish oil results, which in hot or cold water forms a turbid solution.

Yield: 51 g; $n^{20}_D = 1.4779$.
Hydroxyl number (OH-number)=92; p=12.1%.

EXAMPLE 2: (n=1, m=4)

1 g of a 33% strength sodium methylate solution in methanol is added dropwise to a mixture of 13.4 g (0.05 mole) of oleyl alcohol, a small amount of thymolphthalein and 24 g (0.2 mole) of MOP at 0°–20° C. in the course of 15 minutes, whilst cooling. The originally blue solution loses its color on subsequent stirring.

Yield = about 38 g.

The pale yellowish oil has an OH-number of 79. $n^{20}_D = 1.4766$; P=15.7%.

EXAMPLE 3: (n=1, m=8)

13.4 g (0.05 mole) of oleyl alcohol, a small amount of thymolphthalein indicator and 1 g of a 33% strength sodium methylate solution in methanol are mixed and the methanol is stripped off at room temperature under a vacuum of 2.3 mbar. 68.0 g (0.4 mole) of MOP are then added dropwise in the course of 30 minutes, whilst cooling with ice, and at the same time a further 1.8 g of the sodium methylate solution are added dropwise in order to maintain the blue coloration. 63.5 g of an oil results; this oil is initially still blue but after standing for 2 hours at room temperature loses its color of its own accord and gives a clear solution in water. On shaking, the solution shows vigorous foaming. $n^{20}_D = 1.4920$; OH-number = 53; P = 19.5%.

EXAMPLE 4: (n = 1, m = 10)

A small amount of thymolphthalein and 60 g (0.5 mole) of MOP are added to 18.2 g (0.05 mole) of tetrahydro-perfluoro-octanol at room temperature. 2.8 g of a 33% strength solution of sodium methylate in methanol are added dropwise in the course of 15 minutes at 30° C. Hereupon, the temperature rises to 42° C. The solution loses its color after stirring for a further 30 minutes. The colorless oil (81 g) gives a completely clear solution in water. On shaking, the solution foams vigorously. $n^{20}_D = 1.4618$; OH-number = 20; p = 19.1%.

EXAMPLE 5: (n = 1, m = 2)

12.2 g (0.1 mole) of 2-phenyl-ethanol, and a small amount of thymolphthalein are stirred for 1 hour, at 40° C., with 0.24 g (0.01 mole) of sodium hydride. 24 g (0.2 mole) of MOP are then stirred into the mixture in the course of 5 minutes at 5°–10° C. Hereupon, the temperature rises to 50° C. Yield: 37 g. The blue solution loses its color after about 30 minutes. The colorless oil gives a turbid solution after dilution with water at 50° C. $n^{20}_D = 1.5152$; OH-number = 128; P = 16.7%.

EXAMPLE 6: (n = 1, m = 3)

2.7 g of a 33% strength sodium methylate solution in methanol are added dropwise in the course of 12 minutes to a mixture of 6.4 g (0.2 mole) of methanol, a small amount of thymolphthalein and 72 g (0.6 mole) of MOP at 10° C. The blue coloration of the indicator disappears on continuing to stir the mixture. Yield 81 g. $n^{20}_D = 1.4792$; OH-number = 154; P = 22.7%.

EXAMPLE 7: (n = 2, m = 2)

15.5 g (0.25 mole) of ethylene glycol, a small amount of thymolphthalein and 3 g of a 33% strength solution of sodium methylate in methanol are mixed at 20° C. and the methanol is stripped off at 4 mbar. 120 g (1 mole) of MOP are then added dropwise in the course of 15 minutes, whilst cooling. The blue solution loses its color after stirring for a further hour. Yield 138 g.

OH-number = 183; $n^{20}_D = 1.4956$; P = 22.5%.

EXAMPLE 8: (n = 3, m = 1)

27.6 g (0.3 mole) of anhydrous glycerol, a small amount of thymolphthalein indicator and 1.44 g (0.06 mole) of sodium hydride are heated for 60 minutes to 50° C. 108 g (0.9 mole) of MOP are then added to the mixture at 10° C. over 30 seconds, whilst cooling with ice and stirring vigorously. In the course of the addition, the temperature rises to 56° C. in spite of the cooling. After stirring for a further 30 minutes at 30° C., the solution loses its color. Yield 137 g.

The colorless oil has the following data: $n^{20}_D = 1.4762$; OH-number = 305; P = 20.2%.

EXAMPLE 9: (n = 3, m = 3.6)

2.5 g of a 33% strength sodium methylate solution in methanol are added to 5.1 g (0.055 mole) of anhydrous glycerol. The methanol is stripped off at room temperature under 4 mbar. Thereafter 72 g (0.6 mole) of MOP are added dropwise in the course of 20 minutes at 40° C., whilst cooling. Yield of colorless oil: 79 g.

OH-number = 56; P = 23.8%.

EXAMPLE 10: (n = 4, m = 2)

A mixture of 17.0 g (0.125 mole) of pentaerythritol, a small amount of thymolphthalein and 120 g (1 mole) of MOP is heated to 50° C. until a clear solution is obtained. At 30° C., 5 g of a 33% strength solution of sodium methylate in methanol are added dropwise in the course of 30 minutes, whilst cooling. The solution remains an intense blue. It is then stirred for a further hour, in the course of which it loses its color. After cooling the solution, a viscous oil is obtained. $n^{20}_D = 1.5033$; OH-number = 157; P = 21.7%; yield = 142 g.

EXAMPLE 11: (n = 2, m = 2)

17.6 g (0.2 mole) of butene-1,4-diol and a small amount of thymolphthalein are stirred with 0.96 g (0.04 mole) of sodium hydride for 50 minutes at 50° C. 96 g (0.8 mole) of MOP are then added dropwise to the deep blue solution in the course of 50 minutes at 25°–30° C., whilst cooling. On continuing to stir at 20° C., the reaction mixture loses its color. The resulting oil, which has a pale yellow color, shows a refractive index of $n^{20}_D = 1.5002$; OH-number = 163; P = 21.4%; yield = 114.5 g.

EXAMPLE 12: (n = 3, m = 2)

89.3 g (0.666 mole) of 2-methyl-2-oxo-4-methyl-oxaphospholane

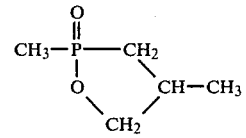

are added to 16.5 g (0.111 mole) of triethanolamine and a small amount of thymolphthalein at 10° C., whilst cooling. During this reaction, there is as yet no significant reaction exothermicity. However, such is the case on dropwise addition of a total of 4 g of a 33% strength sodium methylate solution in methanol in the course of 20 minutes. The blue solution loses its color on subsequent stirring. Yield of colorless oil = 110 g. $n^{20}_D = 1.4838$; P = 18.7%; OH-number = 136.

EXAMPLE 13: (n = 1, m = 2)

96 g (0.8 mole) of MOP are added to 24.4 g (0.4 mole) of monoethanolamine and a small amount of thymolphthalein at 20° C. in the course of 5 minutes, after which 3 g of a 33% strength solution of sodium methylate in methanol are added in the course of 20 minutes at 20°–30° C., whilst cooling. After continuing to stir for 1 hour at 20° C., 123.4 g of a colorless oil of refractive index $n^{20}_D = 1.4915$ result. OH-number = 167; total N = 4.5%; basic N = 4.5%; P = 19.9%.

EXAMPLE 14: (n = 1, m = 1)

5 g of a 33% strength solution of sodium methylate in methanol are added to 52.5 g (0.5 mole) of 2-hydroxyethyl carbamate, a small amount of thymolphthalein and 60 g (0.5 mole) of MOP in the course of 25 minutes at 0°–5° C., whilst cooling thoroughly with ice. After stirring for a further 2 hours, 117.5 g of a colorless oil result. $n^{20}_D = 1.4815$; OH-number = 269; P = 13.0%.

EXAMPLE 15: (n=1, m=2)

The procedure followed is analogous to Example 14, using only 26.3 g (0.25 mole) of 2-hydroxyethyl carbamate. 91 g of a colorless oil result. $n^{20}_D = 1.4863$; OH— number=181; P=16.9%.

EXAMPLE 16: (n=1, m=1)

52 g (0.5 mole) of 2-hydroxyethylurea and a small amount of thymolphthalein are dissolved in 50 g of dimethylformamide at 75° C. 0.72 g (0.03 mole) of sodium hydride are then introduced at 30° C. and the mixture is kept at this temperature for 2 hours, until the sodium hydride has dissolved. 60 g (0.5 mole) of MOP are then added in the course of 5 minutes at 10°–15° C., whilst cooling. The solution remains blue. The dimethylformamide is then distilled off at 100° C. and 4 mbar. 111 g of a viscous oil remain. $n^{20}_D = 1.5032$; OH-number=219; P=13.5%

USE EXAMPLES

EXAMPLE 1

A needle-punched nonwoven carpeting weighing about 780 g per square meter and consisting of a fine denier polyester fiber core and a coarse denier polyamide upper face, in the ratio of 65:35, is treated on a two-roll padder with an aqueous impregnating solution having the following composition:

200 g/l of a reaction product synthesized, analogously to Preparation Example 9, from 1 mole of glycerol and 10.8 moles of 2-methyl-2-oxo-oxaphospholane (P=23.8%), 100 g/l of a 80% strength trimethylolmelamine trimethyl ether, 300 g/l of a 50% strength polymer dispersion consisting of vinyl acetate-ethylene in the ratio of 84:16 and 5 g/l of ammonium chloride. The wet pick-up is 100%. The material is then dried for 20 minutes at 140° C.

The needle-punched felt has very good flame-retardant properties, which are not lost even after 5 shampooings or after several washes under fine fabric conditions at 40°–50° C.

The burning characteristics are tested in accordance with DIN 54,332 "Determination of the burning characteristics of textile floor coverings" and according to DIN 54,333 "Determination of the flame spread rate on textiles".

If the test specimen is finished only with 300 g/l of the copolymer dispersion mentioned in the example, it continues to burn, according to DIN 54,332, after removal of the test flame (15 seconds exposure time); the same is true of the test according to DIN 54,333. After removing the test flame (15 seconds exposure time) the test specimen continues to burn over a broad front. The flame front traverses the test distance of 10 cm in a time of 2 minutes and 54 seconds.

In contrast, the textile goods treated with the impregnating liquor mentioned above does not continue to burn, on removal of the test flame, either according to DIN 54,332 or according to DIN 54,333. In the test, the flame exposure time according to DIN 54,332 is increased from 15 to 30 seconds and 60 seconds. Even after such long flame exposure times the test specimens do not continue to burn after removing the flame.

After 2 or 5 shampooings, continued burning, or burning-away, is not observed either according to DIN 54,332 or according to DIN 54,333. The same picture is found after 3 washes under fine fabric conditions with 2 g/l of a commercial detergent for fine fabrics (duration of each wash: 15 minutes at 40° C.). The test specimens do not continue to burn. According to DIN 54,333, a flame-continuation time of only 30 seconds is found.

The needle-punched felt finished in accordance with the invention has very good resilient properties and shows good unrolling capacity.

Instead of the 50% strength vinyl acetate/ethylene (84:16) polymer dispersion, a 40% strength ethyl acetate/acrylonitrile/N-methylolacrylamide (6:3:1) copolymer dispersion can also be used. The flame-retardant tests show a similar picture.

EXAMPLE 2

A needle-punched nonwoven carpeting, weighing 700 g/m² and consisting of a fine denier polypropylene core with a proportion of about 30% of polyamide fibers, and a coarse denier polypropylene fiber upper face is treated on a two-roll padder with the aqueous impregnating solution described in Example 1.

The wet pick-up is about 100%. The material is then dried for 30 minutes at 130° C.

The needle-punched nonwoven carpeting again has very good permanent flame-retardant properties according to DIN 54,332 and DIN 54,333.

After removing the test flame, the needle-punched nonwoven does not continue to burn, whilst if it has been treated only with 300 g/l of a 50% strength vinyl acetate/ethylene (84:16) polymer dispersion, it burns away, according to DIN 54,333, in 2 minutes 20 seconds.

The needle-punched nonwoven carpeting finished in this way is resilient and exhibits a dry hand.

EXAMPLE 3

A broadloom tufted carpet, 600 g/m², comprising a 6 mm high cut polyamide pile on a base material of needle-punched polypropylene nonwoven is treated with the following pre-coat impregnating solution:

150 parts of a reaction product of 1 mole of glycerol + 10.8 moles of 3-methyl-2-oxo-oxaphospholane (P=23.9%), 75 parts of an 80% strength trimethylolmelamine trimethyl ether, 150 parts of a 50% strength butadiene-styrene (60:40) copolymer dispersion, 280 parts of chalk, 325 parts of a 2% strength methyl-hydroxyethylcellulose solution, and 5 parts of ammonium chloride.

The pre-coat is applied by means of a manually operated doctor and is dried for 20 minutes at 140° C. The dry coating weight is about 600 g/m².

The pile threads are very well bonded in the base fabric and exhibit their original mobility, since the pre-coat impregnating solution has not penetrated into the pile. The tufted carpet, provided with the flame-retardant finish, is intended for fitting in interior spaces such as the luggage trunks of automobiles. It exhibits a flexible and pleasant hand.

The flame-retardant properties of the finished tufted carpet are tested in accordance with DIN 54,333. In comparison, a portion of the tufted material described above is coated, on the manual doctor, with a precoat which does not contain a flame-retardant component. The pile threads are here again bonded to the base fabric with a 50% strength butadiene-styrene (60:40) copolymer dispersion, with the addition of chalk and methyl-hydroxyethylcellulose solution as thickener. The carpet which has not been provided with the flame-retardant finish burns away after removing the test flame. On the other hand, the carpet specimen provided with the flame-retardant finish shows no continuation of burning, or smouldering, after removing the test flame.

The very good flame-retardant effect remains fully preserved even after 3 shampooings.

EXAMPLE 4

Equally good flame-retardant effects are achieved if instead of 150 parts of a 50% strength butadiene-styrene (60:40) copolymer dispersion as the polymer dispersion, a 50% strength vinyl acetate/ethylene (84:16) copolymer dispersion is employed in the finishing liquor as described in Example 3.

The pile threads are again very well bonded in the base fabric. The flame-retardant effect, measured according to DIN 54,333, is excellent and remains preserved even after 4 shampooings.

EXAMPLE 5

The needle-punched nonwoven carpeting described in Example 1 is treated, on a two-roll padder, with the following flame-retardant finishing liquor:

240 g/l of a reaction product, synthesized according to Preparation Example 3, of 1 mole of oleyl alcohol+8 moles of 2-methyl-2-oxo-oxaphospholane (P=19.5%), 120 g/l of an 80% strength trimethylolmelamine trimethyl ether, 300 g/l of a 40% strength ethyl acrylate/acrylonitrile/N-methylolacrylamide (6:3:1) polymer dispersion and 45 g/l of ammonium chloride.

The wet pick-up is about 85%. Following the padding, the material is dried for 25 minutes at 145° C.

The needle-punched nonwoven carpeting has very good flame-retardant properties. Its handle is resilient and dry.

EXAMPLE 6

The needle-punched nonwoven carpeting used in Example 2 is treated, on a two-roll padder, with the following impregnating solution:

200 g/l of a reaction product of 1 mole of glycol with 4 moles of 2-methyl-2-oxo-oxaphospholane (P=22.5%), 100 g/l of an 80% strength trimethylolmelamine trimethyl ether, 250 g/l of a 40% strength ethyl acrylate/acrylonitrile/N-methylolacrylamide (6:3:1) polymer dispersion and 5 g/l of ammonium chloride.

The wet pick-up is about 100%. The material is dried for 20 minutes at 130° C.

A needle-punched nonwoven carpeting having very good flame-retardant properties, a dry hand and very good resilience is obtained.

The flame-retardant properties were tested according to DIN 54,333. After removing the test flame, the test specimen did not continue to burn. This very good flame-retardant effect remained preserved even after 3 shampooings; burning was found to continue for 15 seconds only.

EXAMPLE 7

The needle-punched nonwoven carpeting described in Example 1 was finished with an impregnating solution of the following composition:

250 g/l of a reaction product, synthesized according to Preparation Example 12, of 1 mole of triethanolamine with 6 moles of 2,4-dimethyl-2-oxo-oxaphospholane (P=18.7%), 180 g/l of an 80% strength trimethylolmelamine trimethyl ether, 250 g/l of a 50% strength vinyl acetate/ethylene (84:16) polymer dispersion, and 5 g/l of ammonium chloride.

The method of applying the finish is described in Example 1. The needle-punched nonwoven carpeting exhibits good flame-retardant properties.

EXAMPLE 8

A needle-punched nonwoven carpeting weighing about 700 g per square meter and consisting of a fine denier polypropylene core and a coarser denier polypropylene fiber upper face is treated, on a two-roll padder, with an aqueous impregnating solution which has the following composition:

200 g/l of a reaction product, synthesized according to Preparation Example 10, of 1 mole of pentaerythritol with 8 moles of 2-methyl-2-oxo-oxaphospholane (P=21.7%), 100 g/l of an 80% strength trimethylolmelamine trimethyl ether, 300 g/l of a 50% strength butadiene/styrene (60:40) polymer dispersion, and 5 g/l of ammonium chloride.

The wet pick-up is about 100%. The material is then dried for 20 minutes at 135° C.

The needle-punched nonwoven carpeting has very good flame-retardant properties, which are preserved after several shampooings or wet washes at 40° C.

The burning characteristics are determined in accordance with DIN 54,333 "Determination of the flame spreading rate on textiles". The same needle-punched nonwoven carpeting, finished only with 300 g/l of the 50% strength butadiene/styrene (60:40) polymer dispersion continues to burn over a broad front afte removing the test flame (15 seconds exposure time). 10 cm of the test length are burnt away in 2 minutes 30 seconds. The needle-punched felt with the flame-retardant finish does not continue to burn after removing the test flame; the flames go out after 6 seconds.

EXAMPLE 9

The needle-punched felt described in Example 1 is finished with the following impregnating liquor:

230 g/l of a reaction product, synthesized according to Preparation Example 4, of 1 mole of a perfluoroalkylethanol ($C_6F_{13}$-$C_2H_4$-OH)+10 moles of 2-methyl-2-oxo-oxaphospholane (P=19.1%), 100 g/l of an 80% strength trimethylolmelamine trimethyl ether, 400 g/l of a 50% strength vinyl acetate/ethylene (84:16) polymer dispersion, and 4.5 g/l of ammonium chloride.

The treatment is carried out on a two-roll padder the wet pick-up being about 110%. The material is dried for 25 minutes at 135° C.

The needle-punched felt has very good flameretardant properties, and a resilient handle.

EXAMPLE 10

A textile wall covering which consists of 75% of glass fibers and 25% of polyester fibers is treated with an impregnating solution as described in Example 1. The excess impregnating solution is removed by passing over a steel roller, the backing roller being a rubber roller which is additionally wrapped with a knitted cotton fabric as lapping. The wet pick-up is about 135%. After drying for 20 minutes at 145° C., an excellent textile wall covering which withstands sliding into position, and is flame-retardant, is obtained.

EXAMPLE 11

A needle-punched nonwoven carpeting, as described in Example 1, is treated with the following impregnating solution:

250 g/l of a reaction product, synthesized in accordance with Preparation Example 17, of 1 mole of 2-hydroxyethyl methacrylate and 3 moles of 2-methyl-2-oxooxaphospholane (P=18.3%).

80 g/l of a 50% strength N,N'-dimethylolmethylene-bis-acrylamide solution, 50 g/l of an 80% strength trimethylolmelamine trimethyl ether, 300 g/l of a 50% strength vinyl acetate/ethylene (84:16) copolymer dispersion, and 5 g/l of potassium persulfate.

The wet pick-up on the padder is about 105%. The material is then dried for 28 minutes at 140° C.

The needle-punched nonwoven carpeting exhibits very good flame-retardant properties and a resilient hand. When tested according to DIN 54,333 after 3 shampooings, brief continuation of burning, for 10 seconds, is found after removing the test flame (15 seconds exposure).

EXAMPLE 12

A tufted carpeting having the composition and construction described in Example 3, is treated with the following pre-coat impregnating liquor:

150 parts of a reaction product, synthesized according to Preparation Example 11, of 1 mole of butenediol+4 moles of 2-methyl-2-oxo-oxaphospholane (P=21.4%).

75 parts of an 80% strength trimethylolmelamine trimethyl ether, 200 parts of a 50% strength vinyl acetae/ethylene (84:16) copolymer dispersion, 280 parts of chalk, 300 parts of a 2.5% strength methylhydroxyethylcellulose solution and 5 parts of ammonium chloride.

The pre-coat is applied by means of a manually operated doctor and dried for 25 minutes at 135° C. The dry coating weight is about 650 g/m$^2$.

The tufted carpeting shows a flexible, resilient hand. The pile threads are well bonded in the base fabric. The impregnating solution has not penetrated into the pile. The tufted carpeting has very good flame-retardant properties which withstand several shampooings.

We claim:

1. Organic phosphorus compounds possessing 3-hydroxyalkylphosphinic acid ester groups, of the general formula I

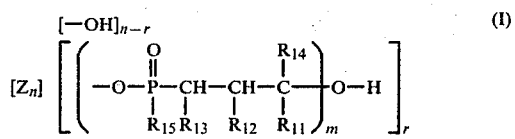

wherein the individual symbols of the above formula I have the following meaning:

n is an integer from 1 to 6, preferably 1 to 4;

r is an integer from 1 to n, that is to say from 1 to 6, and is preferably the same number as n;

m is 1 if r<n, or is a number from 1 to 150, preferably 2 to 10, if r is equal to n;

$R_{11}$, $R_{12}$, $R_{13}$ and $R_{14}$ are identical or different, optionally unsaturated and/or branched, alkyl radicals with 1 to 4 carbon atoms or, preferably, are hydrogen;

$R_{15}$ has the same meaning as $R_{11}$, other than hydrogen, and is preferably ($C_1$–$C_3$)-alkyl, and particularly preferentially methyl;

$Z_n$ is a n-valent radical from the group of straight-chain or branched aliphatic or araliphatic hydrocarbon radicals with 1 to 22, preferably 1 to 8, C atoms, which can optionally be interrupted by up to 2 —S— and/or $NR_2$- radicals, where $R_2$ is ($C_1$–$C_4$)-alkyl, especially methyl, and/or be substituted by fluorine, chlorine or bromine atoms or by optionally unsaturated carboxylic acid ester groups or carboxamide, carbamate or urea groups or by primary, secondary or tertiary amino groups; or is a hydrocarbon radical, containing ether groups, with equivalent weights of up to 8,000, preferably up to 4,000, resulting from oxyethylation and/or oxypropylation of n-valent aliphatic, araliphatic or aromatic hydroxyl compounds, amines and/or monocarboxylic or dicarboxylic acids with 1 to 22, preferably 1 to 10, C atoms, the araliphatic or aromatic radicals being derived from benzene, alkylbenzenes or alkylenebenzenes with up to 18 C atoms, naphthalene, diphenyl, diphenylmethane, diphenylethane or 2,2-diphenylpropane, and being optionally substituted in the nucleus by 1 or 2 methoxy or ethoxy groups, or optionally substituted, preferably up to five times, in the nucleus and/or in the side chains by F, Cl or Br atoms; or is a phosphorus-containing radical of the general formula

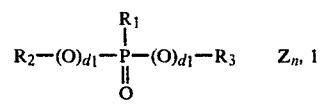

in which the indices $d_1$, independently of one another are 0 and 1 and $R_1$ is alkyl, hydroxyalkyl, optionally ($C_1$–$C_2$)-alkylated or -dialkylated aminoalkyl, halogenoalkyl (preferably Cl-alkyl) with 1 to 3 C atoms, alkenyl with 2 or 3 C atoms or phenyl, which can optionally be substituted by 1 or 2 halogen atoms, preferably Cl or Br, and $R_2$ and $R_3$ have the same meaning as $R_1$, with the restriction that at least one of the radicals $R_2$ or $R_3$ is an alkyl radical with 2-5 C atoms;

or is a phosphorus-containing radical of the formula

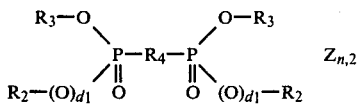

in which $d_1$, $R_2$ and $R_3$ have the same meanings as $Z_{n,1}$ and $R_4$ denotes a straight-chain or branched $(C_1-C_{10})$-alkylene, phenylene or xylylene radical or a radical

where Y is OH or $NH_2$ and $R_5$ is $(C_1-C_3)$-alkyl; or is a phosphorus-containing radical of the general formula

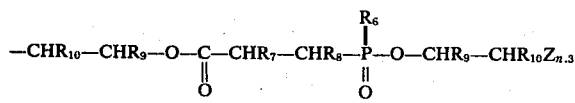

in which $R_6$ denotes a $(C_1-C_4)$-alkyl group which can optionally be substituted, preferably monosubstituted, by halogen, especially chlorine, a cycloalkyl group with up to 8 C atoms, especially cyclopentyl or cyclohexyl, an alkylene group with up to 4 C atoms, especially vinyl and allyl, or a phenyl or benzyl group which is optionally substituted, preferably monosubstituted, disubstituted or trisubstituted, by halogen, preferably chlorine and/or bromine, $R_7$ denotes hydrogen or a $(C_1-C_4)$-alkyl group, preferably methyl, $R_8$ denotes hydrogen or a $(C_1-C_2)$-alkyl group, preferably methyl, but at least one of the radicals $R_7$ and $R_8$ is hydrogen, $R_9$ denotes hydrogen, methyl or chloromethyl and $R_{10}$ denotes hydrogen, methyl or ethyl, preferably hydrogen.

2. Process for the preparation of the phosphorus compounds according to claim 1, wherein 1 mole of a compound of the general formula II $$Z_n(OH)_n \tag{II}$$

is reacted at minus 10° C.–200° C. with 1 to n.25 moles of 2-substituted 2-oxo-oxa-phospholanes of the general formula III

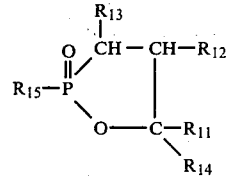

wherein n, $R_{11}$, $R_{12}$, $R_{13}$, $R_{14}$ and $R_{15}$, and $Z_n$, have the meanings given above.

* * * * *